United States Patent [19]

Cardarelli

[11] 4,237,113
[45] Dec. 2, 1980

[54] BIOLOGICALLY ACTIVE INSECTICIDE CONTAINING POLYMERIC FORMULATION

[76] Inventor: Nathan F. Cardarelli, 3261 Brenner Rd., Barberton, Ohio 44203

[21] Appl. No.: 5,173

[22] Filed: Jan. 22, 1979

Related U.S. Application Data

[63] Continuation-in-part of Ser. No. 916,570, Jun. 19, 1978, Pat. No. 4,166,111.

[51] Int. Cl.³ ................... A01N 57/00; A01N 57/26; A01N 47/10
[52] U.S. Cl. ........................................ 424/78; 424/22; 424/83; 424/200; 424/300
[58] Field of Search ............................. 424/78, 83, 22

[56] References Cited

U.S. PATENT DOCUMENTS 3,590,119  6/1971  Cardarelli et al. ............... 424/22
4,012,221  3/1977  Walker et al. ..................... 71/66

OTHER PUBLICATIONS

Chemical Abstract 75: 97577c (1971).

Primary Examiner—Leonard Schenkman
Attorney, Agent, or Firm—Oldham, Oldham, Hudak & Weber Co.

[57] ABSTRACT

An insecticide containing polymeric composition having insecticidal activity against insect pests in the household and agriculture comprises an organic insecticide which is dispersed throughout the polymer matrix as in a monolithic manner. Through the appropriate matrix selection and attractant-porosigen compounds, the insecticide and attractant slowly migrates to the polymer surface whereby various insects, for example, ants, fire ants, cockroaches, silverfish and the larva stage of the various crawling insects that damage fruit trees, nut trees, grapes and other agricultural plants are generally destroyed through contact with said insecticide by moving on or across said polymer surface. The insecticide polymeric composition generally contains either an ethylene-propylene copolymer or a copolymer of ethylene-vinyl acetate. The insecticide can be either O,O-diethyl-O-(2-isopropyl-6-methyl-5-pyrimidinyl) phosphorothiate or 2-(1-methylethoxy) phenol methylcarbamate. The attractant-porosigen compound or agent can be soil oil or lecithin.

23 Claims, No Drawings

BIOLOGICALLY ACTIVE INSECTICIDE CONTAINING POLYMERIC FORMULATION

CROSS-REFERENCE

This application is a continuation-in-part of my earlier application bearing Ser. No. 916,570 filed June 19, 1978 now U.S. Pat. No. 4,166,111 relating to "A Method and Composition for the Long Term Controlled Release of a Non-Persistent Organotin Pesticide From an Inert Monolithical Dispenser."

BACKGROUND OF THE INVENTION

The subject invention relates to synthetic polymers containing a dispersed insecticide. More specifically, the present invention relates to a method of causing the migration of said insecticide to the surface of the synthetic polymer at a continuous and uniform rate sufficient to destroy pest insects by short term contact on said polymer surface. By adjustments of the migration rate, long term insecticide migration is possible. Thus, long term control of the target pest with improved economy and reduced environmental impact over other control methodologies, such as the use of area sprays and the like is possible.

Heretofore, it is known that pesticidal properties can be imparted to polymeric materials by incorporating a pest control agent in said polymer with various additives. U.S. Pat. No. 3,417,181 teaches that organotin pesticides can be dissolved in elastomeric polymers and caused to release through a diffusion-dissolution mechanism in water. Likewise, U.S. Pat. Nos. 3,590,119, 3,426,473, 3,851,053 and 3,639,583 extend the nature of the toxicant used and teach methods of formulation, but in all cases, activity is dependent upon the solubility of the given agent in the polymeric base and release occurring in an aqueous environment. U.S. Pat. No. 4,012,221 teaches that wherein a nonsoluble agent is incorporated in an elastomeric-type polymer, release can be afforded in a water environment if the amount so incorporated of said agent is sufficiently high and a water soluble coleachant is used to regulate the polymer/water interface. Plastic type materials and environments other than water are excluded from the above patents.

It is well known to the compounding art that agents which are not soluble within a polymeric matrix will not generally move at efficient rates through the matrix in that the propulsive force of solution pressure does not exist. Consequently, long term controlled release of nonsoluble agents heretofore has been thought impossible.

One method, now a recognized part of the pesticide polymeric formulation art, relies upon the use of a third phase material through which the pesticides is transmitted to the polymer surface. Specifically, this methodology relies upon the use of a polyvinyl chloride matrix to which is added one or more of several chemicals generically termed plasticizers and one or more pesticides. Since the plasticizing element is soluble to some extent within the polyvinyl chloride matrix, the molecules thereof will gradually flow towards the polymeric material and surface and usually removed from said surface by volatilization or mechanical washing, or other action of a nonchemical nature. If the given pesticide molecules are soluble or dispersable within said plasticizer, said pesticide molecules will migrate in the plasticizer flow and thus reach the surface. In such one well known application described in a number of patents such as U.S. Pat. Nos. 2,956,073, 3,116,201 and 3,318,769, a volatile insecticide is released for several months causing a vapor-induced toxicity to insects in the lethal zone surrounding the dispersing plastic commodity.

A plasticized polyvinyl chloride, prepared as a plastisol, containing a given amount of a toxic agent wherein the amount of said agent reaching the surface is controlled through the lamination of a plastic membrane on that surface is described in U.S. Pat. No. 3,705,938 and others. In this instance, contact poisons move slowly to the polymer dispenser surface controlled by additional means of the regulating laminated membrane, creating a toxic surface lethal, by contact, to insects moving across said surface. A similar technique is used in preparing bactericidal polymers as described in the above-listed U.S. Pat. Nos. 3,705,938 and 3,288,669.

U.S. Pat. No. 3,212,967 teaches that a plastic type polymer can be created which will release a pesticide if the pesticide moiety is chemically bonded to the polymeric backbone and cleavage of said appended moiety can occur.

In contrast, the present invention relates to the use of nonplasticized plastic type polymers that are not solutes for the given pesticidal agent, wherein the pesticidal agent is monolithically dispersed, (that is, generally, each agent molecule is completely enveloped by polymer molecules, as opposed to encapsulation wherein agent molecules are aggregated, and agent migration is through diffusion within said matrix, with the permeability being internally controlled and thus the migration rate is controlled without the use of a laminated surface membrane. Moreover, said polymer composition preferably contains an attractant-porosigen that similarly moves to the matrix/air interface, attracting the specific insect target to that surface with said insecticide eliciting chemotaxis in said insect.

SUMMARY OF THE INVENTION

Therefore, it is an object of the present invention to provide a slow release insecticide contained in a plastic type polymer.

It is another object of the present invention to provide a slow release insecticide contained in a plastic type polymer, as above, wherein said insecticide is slowly diffused through said polymer for release over an extended period of time.

It is a further object of the present invention to provide a slow release insecticide contained in a plastic type polymer, as above, wherein said polymer is a copolymer of ethylene and propylene, or a copolymer of ethylene and vinyl acetate.

It is an additional object of the present invention to provide a slow release insecticide contained in a plastic type polymer, as above, wherein a coleachant filler is utilized as a porosigenic agent.

It is still another object of the present invention to provide a slow release insecticide contained in a plastic type polymer, as above, wherein an attractant is utilized and also serves as a porosigen.

It is a still further object of the present invention to provide a slow release insecticide contained in a plastic type polymer, as above, wherein said attractant-porosigen is soy oil or lecithin.

It is an additional object of the present invention to provide a slow release insecticide contained in a plastic type polymer, as above, wherein said insecticide migrates outwardly to the surface through the pores created by said attractant-porosigen and/or said coleachant.

It is yet another object of the present invention to provide a slow release insecticide contained in a plastic type polymer, wherein said insecticide is 0,0-diethyl-0-(2-isopropyl-6-methyl-5-pyrimidinyl)phosphorothiate or 2-(1-methylethoxy) phenol methylcarbamate.

Generally, a slow release insecticide-containing polymer composition, comprises: 100 parts by weight of a polymer selected from the class consisting of an ethylene-propylene copolymer, an ethylene-vinyl acetate copolymer, and combinations thereof, said ethylene-vinyl acetate copolymer having a weight average molecular weight of from about 40,000 to about 400,000 and the amount of said ethylene in said copolymer ranging from about 60 to about 95 percent by weight, said ethylene-propylene copolymer having a weight average molecular weight of from about 50,000 to about 250,000, and the amount of said ethylene in said copolymer ranging from about 30 to about 80 percent by weight; and an insecticide.

Additionally, a process for dispensing an insecticide from an insecticide-containing polymer composition over a period of time, comprises the steps of: mixing 100 parts by weight of a polymer selected from the class consisting of an ethylene-propylene copolymer, an ethylene-vinyl acetate copolymer, and combinations thereof, with an insecticide; the amount of ethylene in said ethylene-propylene copolymer ranging from about 30 percent to about 80 percent by weight, the amount of ethylene in said ethylene-vinyl acetate copolymer ranging from about 60 to about 95 percent by weight, the weight average molecular weight of said ethylene-propylene copolymer ranging from about 50,000 to about 250,000, the weight average molecular weight of said ethylene-vinyl acetate copolymer ranging from about 40,000 to about 400,000; forming an article from said mixture, and applying said article to a desired environment so that said insecticide gradually migrates into the article surface and is slowly released.

DESCRIPTION OF THE PREFERRED EMBODIMENTS

A sustained release trialkyl or triaryl organotin composition has been found to be very effective against mosquito larva and against molluscan hosts of various trematode parasites and, in some cases, the aquatic larval forms of such parasites, as well as other aquatic pests, when utilized with a specific polymer matrix and coleachant system. The compositions involved permit a long duration controlled release of the said organotin in ultralow aggregate concentrations in water that result in the gradual accumulation of said agents within the responsive target pest tissues, chronic intoxication and eventual mortality. However, it is believed from empirical evidence that the halogenated trialkyl or triaryl organotins absorbed by or ingested by target species are both proteolytic and antimorphogenetic, and because of the nature of such mechanisms leading to mortality for the target to acquire resistance would necessitate evolving new proteins and peptide linkages.

The pesticide composition consists of halogenated trialkyl organotin or a triaryl organotin possessing either low or very low water solubility and no thermoplastic solubility, bound and uniformly dispersed in a thermoplastic ethylene-vinyl acetate copolymer, wherein also uniformly dispersed is an inert material of moderate or low water solubility that serves a porosigenic function. The porosigen is a coleachant; but, unlike the elastomer toxicant system taught in U.S. Pat. No. 4,012,221, functions only to induce and enhance porosity within the matrix and has no function as an interfacial pH regulant. The organotin toxicant is monolithically dispersant in association with the porosity enhancing coleachant.

The specific halogenated trialkyl or triaryl organotin compounds of the present invention contain preferably an alkyl group having from 1 to 8 carbon atoms, preferably from 3 to 6 carbon atoms, with butyl being highly preferred. The aryl group is a substituted phenyl compound such as an alkyl substituted phenyl or an ester substituted phenyl such as phenyl acetate, wherein the alkyl or ester group contains from 1 to 6 carbon atoms. Moreover, phenyl salts may be utilized.

The alkyl organotin compounds are halogenated with fluorine, chlorine, bromide, or iodine with fluorine being preferred. Thus, the preferred compound of the present invention is tributyltin fluoride. Desirably, triphenyltin fluoride can also be used. The solubility of the halogenated organotin compounds in a thermoplastic matrix or a binder is nil, as noted, and very low in water; that is, approximately 3 parts per million by weight or less. The amount of halogenated organotin compound utilized by weight per 100 parts of polymer matrix binding agent ranges from about 25 parts to about 75 parts, with from about 45 parts to 70 parts being preferred. Naturally, smaller or higher amounts may be utilized, but these ranges result in very effective pest-toxicant thermoplastic matrixes.

The polymer matrix or binding agent of the present invention relates to ethylene-vinyl acetate copolymers since they have been found to possess the ability to bond and release halogenated organotin compounds. Such copolymers are readily available in commerce and the amount by weight of the ethylene repeating units, based upon the total weight of the copolymer, ranges from about 60 percent to about 95 percent with a range of from about 80 percent to about 93 percent being preferred. The molecular weight of the copolymer generally ranges from about 40,000 to about 300,000. Desirably, the copolymer has as ASTM Test #D1238 melt flow index of from about 7 to about 10 and a Vicat softening point of from about 70° C. to about 95° C. Since, apparently, the ethylene repeating units in the copolymer act as a regulator with regard to pore size, higher amounts of the ethylene constituent will result in slower release times.

Moreover, in order to promote long release duration, it has been found useful, although not necessary, to blend the ethylene-vinyl acetate copolymer with a polyethylene, especially low density polyethylene having a melt flow index similar to said ethylene-vinyl acetate copolymer and a molecular weight of from about 100,000 to about 400,000. Thus, depending upon the rate of release, various amounts of low density polyethylene may be utilized. Generally, to obtain desirable release rates, the amount of homopolyethylene utilized may range from about 30 percent to about 75 percent and, preferably, from about 40 percent to about 60 percent by weight, based upon the total weight of the blend of the ethylene-vinyl acetate copolymer and the polyethylene.

A number of moderate or low solubility compounds can be utilized as a porosity-inducing agent. By moderate or low solubility, it is meant that the solubility is 0.01 grams per 100 rams of water or less. The porosity-inducing agent or coleachant is generally an alkaline earth metal salt or oxide having low water solubility. Specific examples of coleachants include magnesium carbonate, magnesium bicarbonate, magnesium sulfate, magnesium nitrate, magnesium nitrite, magnesium phosphate, magnesium oxide, calcium carbonate, calcium bicarbonate, calcium sulfate, calcium nitrate, calcium nitrite, calcium phosphate and to a lesser desirability, barium carbonate, barium bicarbonate, barium sulfate, barium nitrate, barium nitrite, barium phosphate, barium oxide, beryllium carbonate, beryllium bicarbonate, beryllium sulfate, beryllium nitrate, beryllium nitrite, beryllium phosphate, and beryllium oxide. Calcium carbonate is highly preferred. The amount of coleachant generally varies from about 15 parts to about 70 parts by weight based upon 100 parts of said polymer matrix (that is, said copolymer or said blend of said polyethylene and said copolymer) and, preferably, from about 25 to about 60 parts.

The composition can contain, in addition to the abovementioned necessary components, various well known and conventional additives to enhance dispersion, add color, aid in processing, or to alter the density. For example, should a composition be desired to sink, any composition having a specific gravity greater than 1 may be added in the necessary amounts to render the overall specific gravity of the material to be greater than 1. Naturally, a non-reactive, relatively inert and non-polluting or detrimental compound to the environment is desired such as silicon dioxide or the like. An example of a dispersant to aid in establishing a uniformed distribution of the organotins such as the tributyltin fluoride compound is zinc stearate in suitable amounts.

In order to form a suitable thermoplastic dispenser which releases suitable amounts of an organotin pesticide through a coleachant system, it is desirable that the particle sizes of the various components be relatively small. For example, it is desirable that the organotin compounds have a Tyler mesh size of roughly 200 or greater (i.e., a particle size smaller than 200 mesh). Accordingly, a particle size range for the coleachant is generally the same. The particle size of the ethylene-vinyl acetate copolymer or the blend of polyethylene and the ethylene-vinyl acetate copolymer is about 60 to 100 Tyler mesh.

The pesticide is prepared by mixing the halogeneated organotin compound with the polymer matrix and the coleachant in suitable proportions as indicated above in any conventional mixing apparatus along with the various additives such as colorants, dispersants, and the like. The mixture is then coalesced by heating and is partitioned for use in any suitable size or shape, for example, pellet, chip, ribbon or ribbon form. For example, the mixture may be added to a conventional extruder where it is molded at about 170° C. to about 190° C. in a suitable form such as a rod, which may be cut up into appropriate pellet sizes.

According to the concepts of the present invention, in lieu of the organotin pesticide, a specific class of insecticide is utilized and distributed upon a non-water surface as in the form of a tape or ribbon so that insects which contact or crawl across the polymer surface containing the insecticide are generally destroyed. The insecticide-containing polymeric compound contains a polymer matrix made from a copolymer of ethylene and vinyl acetate as set forth above. Additionally, an ethylene-propylene copolymer can also be utilized. Preferably, the insecticide-containing composition has an attractant-porosigen which renders it much more efficient in not only luring insects to the composition, but also in aiding in the release of the insecticide therefrom. Moreover, the coleachant compounds set forth above may be utilized to increase the free volume within the polymer matrix and afford easier movement of the insecticide molecules to the surface of the compound. The slow release insecticide composition of the present invention may be utilized wherever required to protect man and his possessions, food stuffs, and agricultural items from insect attack as in a household, dependent structures whether frequented by man or his domestic animals, or food storage facilities such as silos, warehouses, grain elevators, and the like.

The polymer matrix utilized with the insecticide composition are the copolymers of ethylene-vinyl acetate and of ethylene-propylene. Considering the ethylene-vinyl acetate copolymer, it is the same as described hereinabove except that the preferred amount of ethylene in the copolymer ranges from about 80 percent to about 94 percent. Moreover, the weight average molecular weight range is from about 40,000 to about 400,000 with a preferred range being from about 75,000 to about 300,000. The melt flow index generally ranges from about 6 to 12 with an index of from about 7 to 11 being preferred.

Considering the ethylene-propylene copolymer it has a weight average molecular weight range of from about 50,000 to about 250,000 with a preferred range of from about 100,000 to about 200,000. The percent by weight of the ethylene portion can normally vary from 30 percent to about 80 percent and preferably from about 45 to about 75 percent. The melt flow index of the copolymer ranges from about 15 to about 45 and preferably from about 20 to about 32, according to ASTM Test #D1238 at 190° C., 21600 gm,gm/10 minutes. The density of this copolymer can range from about 0.80 to about 0.92 g/cc and preferably from about 0.85 to 0.89 g/cc. A specific example of an ethylene-propylene copolymer is Vistalon 702, manufactured by Exxon Chemical Company. Blends of the two copolymers in any proportion may also be utilized.

It has further been discovered that the utilization of the copolymers of the present invention with coleachants enhance free volume within the polymer matrix and afford easier movement of the insecticide molecules. Generally, the coleachant is any compound which preferably is not harmful to the environment and which is inert, that is will not react with any of the components of the polymeric composition. One such class is the coleachants set forth above, that is the various above-listed salts of the alkaline earth metals. Of this class, magnesium carbonate and barium carbonate are preferred with calcium carbonate being highly preferred. Additionally, various other metals may be utilized such as iron, nickel, zinc, tin, silver and the like. The anion portion of the salt may generally be any negative charge entity charge as the various carbonates, the various nitrates, nitrites, or nitrides, the various sulfates, sulfites, or sulfides, the various phosphates, phosphites, or phosphides, including the ortho, pyro, hypo, variations thereof, and the like. Generally, the sulfates, sulfites and sulfides are preferred as anions, with carbonates being highly preferred. Moreover, as noted above, the anion may be an oxide of the metal. Specific examples of coleachants include magnesium carbonate, magnesium sulfide, magnesium phosphide, magnesium oxide, calcium carbonate, calcium nitride, calcium oxide, calcium phosphate, calcium phosphite, calcium sulfide, calcium sulfite, barium carbonate, barium nitride, barium peroxide, barium phosphate, barium sulfate, barium sulfite, iron carbonate, iron sulfate, iron sulfide, iron sulfite, nickel carbonate, nickel sulfide, zinc carbonate, zinc oxide, zinc sulfide, zinc sulfite, tin sulfide, tin oxide, silver carbonate, silver oxide, silver sulfite, lithium phosphate, beryllium oxide, strontium carbonate, strontium sulfate, and strontium sulfite. Magnesium, strontium and barium carbonates are preferred with calcium carbonate being highly preferred.

The amount of the inert fillers ranges from about 0.1 to 25 parts by weight per 100 parts of polymer and preferably from about 4 to about 16 parts.

An important aspect of the present invention relates to the discovery that certain specific attractants not only serve to attract various insects, but also serve as a porosigen so that a permeation path is provided so that the insecticide may conveniently diffuse towards the polymer composition surface. Such attractant-porosigen agents can be used without the need for any inert filler and are highly preferred in the present invention.

The concomitant use of an attractant-porosigen agent enhances the performance of the slow release compound by enticing the target pest insect to the polymer composition. Moreover, it is well recognized that delivering the target insect to the insecticide results in a more efficient use in that much less pesticide is required to achieve a desired result. The polymer composition also is less hazardous to the environment than dispersing the insecticide on a wide area basis such as a dust or spray which affects all susceptible nontarget biota within the treated area. Still another advantage is the fact that an attractant-porosigen method does not require the presence of toxic vapors at the composition surface.

Various attractant-porosigen agents can be utilized and include such effective and preferred agents as soy oil and lecithin. Generally, the soy oil is used pure, that is 100 percent soy oil, or less desirably mixed with some other compound or oil. The amount by weight of the soy oil or lecithin generally ranges from about 2 to about 25 per 100 parts of copolymer and preferably from about 4 to about 16 parts.

Although the attractant-porosigen is generally utilized by itself, at times it may be desirable to use the above-discussed inert compounds to create voids in the matrix.

Depending upon the type of insecticide utilized, the amount and type of porosigen-attractant or coleachant porosigen, the amount and type of insecticide utilized, and the size and shape of the insecticide-containing polymer, the slow release affected thereby can vary over a time period of a couple days or several days, to several months, and even to a couple of years.

The insecticide generally may be any compound which is compatible with, but not soluble in, the plastic polymer matrix and wherein the insecticide functions as a contact toxicant target insects that crawl, creep, or otherwise traverse or contact the polymeric composition surface. Moreover, the insecticide compound must not be altered physically or chemically under the necessary processing conditions. The insecticide is desirably monolithically dispersed within the polymer matrix and must be defusible through the matrix either in a liquid, vapor or solid form and yet held or retained at the surface of the polymer composition or article. Specific examples of two preferred insecticides are O,O-diethyl-O-(2-isopropyl-6-methyl-5-pyrimidinyl)phosphorothioate or 2-(1-methylethoxy)phenol methylcarbamate. The former is sold as a 50 weight percent powder in combination with an inert carrier under the trademark of Diazinon, manufactured by the Ciba-Geigy Corporation of Greensboro, N.C. The latter is sold as a 70 weight percent concentrated powder with inert ingredients under the trademark of Baygon, manufactured by the Mobay Chemical Corporation of Kansas City, Miss. The amount by weight of O,O-diethyl-O-(2-isopropyl-6-methyl-5-pyrimidinyl)phosphorothioate and of 2-(1-methylethoxy)phenol methylcarbamate pure insecticide (100 percent) ranges from about 0.2 parts to about 40 parts, desirably from about 2 parts to about 35 parts, and preferably from about 5 parts to about 30 parts per 100 parts of copolymer.

The slow release insecticide-polymer composition of the present invention may be prepared in any conventional manner. For example, the polymer, the insecticide, and the attracantporosigen, or the less desirable coleachant, if any, can all be added to an extruder and extruded as in a thin plastic strip. Of course, the composition may be made into any shape or form as by sheeting, pelletizing, molding, and the like, and applied in any manner. Thus, strips or pellets may be placed at or near areas frequented by the target insects. Moreover, a tape or strip of the material may be placed around the storage area as well as around fruit and nut trees or silos so that crawling insects are thereby destroyed. Protection against flight insects may be afforded through the use of attractant-porosigen agents.

Moreover, small amounts (that is a trace to one or two parts) of various specialty-type compounds may be utilized to increase the effectiveness of a slow release insecticide polymer composition. For example, small amounts of zinc stearate, i.e., 0.2 to about 10 or 20 parts may be utilized since it helps to disperse the insecticide. Additionally, small amounts of carbon black, i.e., from about 0.2 to about 10 parts by weight may be utilized as a regulant.

The slow release insecticide polymer composition compounds of the present invention may be used in any form or shape in any location with regard to abating or completely destroying particular insects. For example, a slow release insecticide composition of the present invention utilizing O,O-diethyl-O-(2-isopropyl-6-methyl-5-pyrimidinyl)phosphorothioate is safe from an environmental standpoint and yet is generally recognized as a broad spectrum insecticide with over 60 uses listed. Thus, by way of example, it may be utilized to destroy aphids, ants, ticks, horseflies, and the like, as well as to protect various fruits, vegetables, grains, and the like, such as nut trees, corn, cotton, tomatoes, alfalfa, wheat and rye. Similarly, a slow release formulation of the present invention utilizing Baygon as an insecticide may be utilized to control mosquitos, crickets, grasshoppers, ticks, aphids, grains, and the like. Moreover, the compounds of the present invention are very effective in destroying cockroaches and ants.

The invention will be better understood by reference to the following example.

| INGREDIENT | RECIPES A-G | | | | | | | |
|---|---|---|---|---|---|---|---|---|
| | CONTROL | A | B | C | D | E | F | G |
| Ethylene-propylene copolymer[1] | 69.0 | 69.0 | — | 84.0 | 74.0 | 69.0 | — | — |
| Ethylene-vinyl acetate copolymer[2] | — | — | 68.8 | 1.0 | 1.0 | — | 84.0 | 76.0 |
| Zinc Stearate | 1.0 | 1.0 | 1.0 | 1.0 | 1.0 | 1.0 | 1.0 | 1.0 |
| Diazinon 50 percent w.p.[3] | — | 20.0 | — | 10.0 | 20.0 | 10.0 | 10.0 | 10.0 |
| Baygon 70 percent w.p.[4] | — | — | 15.2 | — | — | — | — | — |
| Soy Oil | 10.0 | 10.0 | 10.0 | — | — | 10.0 | 5.0 | 10.0 |
| Lecithin | — | — | — | 5.0 | 5.0 | — | — | — |
| Calcium Carbonate | — | — | — | — | — | 10.0 | — | — |
| Carbon Black | — | — | — | — | — | — | — | 3.0 |

[1] Vistalon 702 ™ manufactured by Exxon Chemical Co., an ethylene-propylene copolymer having a density of 0.87 g/cc, a melt flow index at 190° C. of 27.

[2] Microthene MU763, manufactured by U.S.I. Chemicals, ethylene-vinyl acetate copolymer having a 9 percent vinyl acetate content, a melt flow index of 9.0, and a density of 0.926 g/cc.

[3] O,O-diethyl-O-(2-isopropyl-6-methyl-5-pyrimidinyl)phosphorothiate, used as a 50 percent powder (50 percent Diazinin in an inert carrier) or as the technical grade as supplied by the Ciga-Geigy Corp. of Greensboro, North Carolina.

[4] 2-(1-methylethoxy)phenol methylcarbamate used as a 70 percent powder in an inert carrier, as supplied by the Mobay Chemical Corp., of Kansas City, Missouri.

After processing as a strip material, various target insects were exposed to a 3-inch × 1-inch section of said strip. The test criterion used is the $LT_{50}$, the intervening time to 50 percent mortality of the test population and the $LT_{100}$, the intervening time to 100 percent mortality of the test population.

Five specific tests were performed with various pest insects.

1. The aforementioned test strip is placed in a 12-inch × 6-inch rectangular container 5 inches deep. Water and food stuffs are provided ad libidum. Ten test insects are placed therein and mortality noted at 24-hour intervals, or less.

2. The second test is similar to the first save that no food stuff is added, thus compelling the said test insect to attempt ingestion or ingest portions of the biologically active strip. When soy oil or lecithin is available within said strip, positive chemotaxis is noted and said insects move to said strip and ingest the surface accumulations (attractant+pesticide).

3. Test insects are placed on said biologically active strip for 10 seconds each and one minute each, removed to nontoxic quarters, and observed periodically for mortality.

4. A phototropic test is also used with those species atropic of light. The test container similar to that of test 1 is maintained ½ dark and ½ light. The bait strip is placed in the lighted portion. These insects, water and food stuffs are placed in a darkened portion. When attraction is present, test insects will venture from the preferred dark section to the non-preferred light section with a view towards ingestion of the strip perceived as a foodstuff.

5. In order to assay the contact toxicity of said formulations, as opposed to vapor toxicity, if indeed any exists, test containers of large air volume are used. Plastic "wading pools" 3 feet in diameter by 0.75 foot in depth are so utilized. Total surface area available for insect movement is 9717 cm². The bioactive strip covers 0.198 percent of said area. Air movement is free and unhindered.

TABLE I

TEST RESULTS: BAIT FORMULATIONS
*Blatella germanica* (German Cockroach)
BAIT EVALUATIONS: $LT_{100}$

| FORMULATION | | With Available Food | | Without Food Supply | | 10 Second Exposure | | 1 Minute Exposure | | Prototropic Test | | Large Volume Test | |
|---|---|---|---|---|---|---|---|---|---|---|---|---|---|
| A | $LT_{50} =$ | 1 | day | 1 | day | 1 | day | 1 | day | 1 | day | 2 | days |
| | $LT_{100} =$ | 2 | days | 2 | days | 3 | days | 1 | day | 2 | days | 5 | days |
| B | $LT_{50} =$ | 1 | day | 2 | days | 6+ | days | 14 | days | 2 | days | 2 | days |
| | $LT_{100} =$ | 8 | days | 6 | days | 6+ | days | 30+ | days | 10 | days | 17 | days |
| C | $LT_{50} =$ | 4 | days | 1 | day | 7 | days | 7 | days | 2 | days | 5 | days |
| | $LT_{100} =$ | 6 | days | 3 | days | 10+ | days | 10+ | days | 2 | days | 14 | days |
| D | $LT_{50} =$ | 2 | days | 1 | day | 1 | day | 1 | day | 2 | days | 2 | days |
| | $LT_{100} =$ | 3 | days | 3 | days | 1 | day | 1 | day | 2 | days | 12 | days |
| E | $LT_{50} =$ | 1 | day | 1 | day | 1 | day | 1 | day | 1 | day | 4 | days |
| | $LT_{100} =$ | 4 | days | 2 | days | 1 | day | 1 | day | 3 | days | 7 | days |
| F | $LT_{50} =$ | 1 | day | 1 | day | 2 | hours | 1 | hour | 6 | hours | 2 | days |
| | $LT_{100} =$ | 4 | days | 1 | day | 3 | hours | 3 | hours | 1 | day | 7 | days |
| G | $LT_{50} =$ | 6 | hours | 1 | day | 4 | days | 6 | hours | 6 | hours | 3 | days |
| | $LT_{100} =$ | 1 | day | 2 | days | 6+ | days | 14 | hours | 1 | day | 7 | days |
| Control* | $LT_{50} =$ | 30+ | days | 30+ | days | 30+ | days | 30+ | days | 30+ | days | 30+ | days |
| | $LT_{100} =$ | 30+ | days | 30+ | days | 30+ | days | 30+ | days | 30+ | days | 30+ | days |

*Control tests are discontinued after 30 days.

TABLE II

FORMICA FUSCA (BLACK ANT)
LT$_{50}$ and LT$_{100}$ BAIT EVALUATIONS

| COMPOUND | | With Available Food | | Without Food Supply | | 10 Second Test | | 60 Second Test | | Large Volume Test | |
|---|---|---|---|---|---|---|---|---|---|---|---|
| A | LT$_{50}$ = | 8 | hours | 2 | hours | 1 | hours | 0.5 | hours | 8 | hours |
|   | LT$_{100}$ = | 24 | hours | 24 | hours | 2 | hours | 1 | hour | 24 | hours |
| B | LT$_{50}$ = | 10 | hours | 4 | hours | 3 | hours | 2 | hours | 13 | hours |
|   | LT$_{100}$ = | 48 | hours | 24 | hours | 24 | hours | 24 | hours | 24 | hours |
| C | LT$_{50}$ = | 3 | hours | 2 | hours | 12 | hours | 1 | hour | 6 | hours |
|   | LT$_{100}$ = | 24 | hours | 12 | hours | 24 | hours | 2 | hours | 24 | hours |
| D | LT$_{50}$ = | 2 | hours | 1.5 | hours | 0.2 | hours | 0.1 | hours | 4 | hours |
|   | LT$_{100}$ = | 6 | hours | 4 | hours | 0.5 | hours | 2 | hours | 18 | hours |
| E | LT$_{50}$ = | 0.5 | hours | 0.5 | hours | 0.25 | hours | 0.1 | hours | 4 | hours |
|   | LT$_{100}$ = | 3 | hours | 3 | hours | 0.5 | hours | 0.5 | hours | 16 | hours |
| Control* | LT$_{50}$ = | 10+ | days | 5+ | days | 10+ | days | 10+ | days | 5+ | days |
|   | LT$_{100}$ = | 10+ | days | 5+ | days | 10+ | days | 10+ | days | 5+ | days |

*Control tests were discontinued after five and 10 days, respectively.

In order to demonstrate longevity as well as efficacy of said formulations, said materials were suspended in circulating air at 70° F. for varying periods of time and re-evaluated in said tests. After 30 days, results were essentially identical. At 120 days, the LT$_{50}$ and LT$_{100}$ had increased by several days, indicating a finite biologically effective life.

EXAMPLE 2

Although subject materials containing an attractant tend to provide greater efficacy, the gradual movement of non-volatile pesticides by diffusion to the polymer-/air interface creates a biologically active surface. Upon passage of said surface by the target insect, minute quantities of said pesticide are contacted to the physiological detriment of said insect. Provided contact time is sufficient, mortality ensues. Illustrative recipes for such formulations are provided below, wherein an attractant-porosigen was not utilized, but carbon black was utilized as a porosigen. The materials were processed as set forth in Table III.

| INGREDIENT | 1 | 2 | 3 | 4 | 5 | 6 | CONTROL |
|---|---|---|---|---|---|---|---|
| Ethylene-propylene[1] copolymer | — | — | 90.9 | — | 79.0 | 67.0 | — |
| Ethylene-vinyl acetate[2] copolymer | 94.5 | 94.0 | — | 90.4 | — | — | 94.5 |
| Zinc Stearate | 1.0 | 1.0 | 1.0 | 1.0 | 1.0 | 1.0 | 1.0 |
| Carbon black[3] | 0.5 | 1.0 | 5.0 | 1.0 | — | 2.0 | 0.5 |
| Diazinon - 50% w.p.[4] | 4.0 | 4.0 | 4.0 | — | 20.0 | 20.0 | — |
| Baygon - 70% w.p.[5] | — | — | — | 7.6 | — | — | — |
| Calcium carbonate | — | — | — | — | — | 10.0 | — |

[1]Vistalon 702 IM manufactured by Exxon Chemical Co., an ethylene-propylene copolymer having a density of 0.87 g/cc, a melt flow index at 190° C. of 27.
[2]Microthene MU763 manufactured by U.S.I. Chemicals, ethylene-vinyl acetate copolymer having a 9 percent vinyl acetate content, a melt flow index of 9.0, a density of 0.926 g/cc.
[3]Carbon black particle size 40 to 70 mm with 60 preferred.
[4]O,O-diethyl-O-(2-isopropyl-6-methyl-5-pyrimidinyl)phosphorothiate, used as a 50 percent powder (50 percent Diazinin in an inert carrier) or as the technical grade as supplied by the Ciba-Geigy Corp., of Greensboro, North Carolina.
[5]2-(1-methylethoxy)phenol methylcarbamate used as a 70 percent powder in an inert carrier, as supplied by the Mobay Chemical Corp., of Kansas City, Missouri.

TABLE IV

BLATELLA GERMANICA (COMMON COCKROACH)

| FORMULATION | | WITH FOOD SUPPLY | | NO FOOD SUPPLY | | 10 SECOND TEST | | 1 MINUTE TEST | | PHOTO-TROPIC TEST | | LARGE VOLUME TEST | |
|---|---|---|---|---|---|---|---|---|---|---|---|---|---|
| 1 | LT$_{50}$ | 2 | days | 2 | days | 13+ | days[1] | 13+ | days | 2 | days | 4 | days |
|   | LT$_{100}$ | 7 | days | 5 | days | 13+ | days | 13+ | days | 5 | days | 8 | days |
| 2 | LT$_{50}$ | 2 | days | 2 | days | 13+ | days | 13+ | days | 5 | days | 7 | days |
|   | LT$_{100}$ | 7 | days | 8 | days | 13+ | days | 13+ | days | 8 | days | 12 | days |
| 3 | LT$_{50}$ | 3 | days | 3 | days | 13+ | days | 2 | days | 2 | days | 6 | days |
|   | LT$_{100}$ | 5 | days | 5 | days | 13+ | days | 8 | days | 7 | days | 10 | days |
| 4 | LT$_{50}$ | 3 | days | 2 | days | 13+ | days | 8 | days | 4 | days | 9 | days |
|   | LT$_{100}$ | 5 | days | 3 | days | 13+ | days | — | | 13+ | days | — | |
| 5 | LT$_{50}$ | 3 | days | 1 | day | 10 | days | 8 | days | 1 | day | 3 | days |
|   | LT$_{100}$ | 6 | days | 4 | days | 13+ | days | — | | 2 | days | 14 | days |
| 6 | LT$_{50}$ | 1 | day | 1 | day | 13+ | days | 9 | days | 1 | day | 3 | days |
|   | LT$_{100}$ | 4 | days | 4 | days | 13+ | days | — | | 2 | days | 9 | days |
| Controls[2] | LT$_{50}$ | 30+ | days | 30+ | days | 30+ | days | 30+ | days | 30+ | days | 30+ | days |
|   | LT$_{100}$ | 30+ | days | 30+ | days | 30+ | days | 30+ | days | 30+ | days | 30+ | days |

[1]Discontinued test after 13 days.
[2]Discontinued test after 30 days.

TABLE V

FORMICA FUSCA (BLACK ANT)
$LT_{50}$ AND $LT_{100}$ BIOASSAY DETERMINATION

| Material | | With Food Available | | No Food Available | | 10 Second Test | | 1 Minute Test | | Large Volume Test | |
|---|---|---|---|---|---|---|---|---|---|---|---|
| 1 | $LT_{50}$ = | 3 | hours | 6 | hours | 1.5 | hours | 0.4 | hours | 24 | hours |
|   | $LT_{100}$ = | 5 | hours | 12 | hours | 3 | hours | 0.6 | hours | 72 | hours |
| 2 | $LT_{50}$ = | 2.5 | hours | 8 | hours | 6 | hours | 0.3 | hours | 24 | hours |
|   | $LT_{100}$ = | 10 | hours | 24 | hours | 48 | hours | 0.5 | hours | 72 | hours |
| 3 | $LT_{50}$ = | 7 | hours | 1.5 | hours | 30 | hours | 6 | hours | 20 | hours |
|   | $LT_{100}$ = | 24 | hours | 4 | hours | 48 | hours | 12 | hours | 48 | hours |
| 4 | $LT_{50}$ = | — | | — | | 20 | hours | 4 | hours | — | |
|   | $LT_{100}$ = | — | | — | | 48 | hours | 6 | hours | — | |
| 5 | $LT_{50}$ = | 1.5 | hours | 3 | hours | 17 | hours | — | | 24 | hours |
|   | $LT_{100}$ = | 4 | hours | 6 | hours | 44 | hours | — | | 72 | hours |
| 6 | $LT_{50}$ = | 3 | hours | 2 | hours | 0.5 | hours | — | | 24 | hours |
|   | $LT_{100}$ = | 10 | hours | 4 | hours | 1 | hour | — | | 72 | hours |
| Control | $LT_{50}$ = | 7+ | days | 5+ | days | 7+ | days | 7+ | days | 7+ | days |
|   | $LT_{100}$ = | 7+ | days | 5+ | days | 7+ | days | 7+ | days | 7+ | days |

In order to evaluate the mechanism through which the target insect is mortally affected by the invention, strips were suspended in circulating air at room temperature and periodically weighed over a 4-month period. Weight loss would be indicative of pesticide loss through volatility. Baygon, containing formulations so evaluated, was found to have less than 0.2 percent decrease in weight over the exposure period indicating essentially no volatilization or an extremely low volatilization of the pesticide. Formulations incorporating Diazinon and so tested over a 4-month evaluatory period showed generally less than 0.4 percent total weight loss indicating essentially a negligible loss of toxicant through volatility. Since toxicant vapor content at the air/strip interface is so low as to likely preclude mortality, it is obvious that the target pest contacts said toxicant in the solid form that has gradually migrated to the surface. Microscopical examination of the insect on the invention surface shows considerable oral activity and preening of the limbs. The preening or cleansing action is periodic and not confined just to time spent in transit of the test strip, but continues for some time after the target has left said strip. Ingestion of surface material on the bait strips was observed.

While in accordance with the patent statutes, the preferred embodiments and best mode of the invention have been presented, the scope of the invention is set forth in the attached claims.

What is claimed is:

1. A slow release insecticide-containing polymer composition for distribution upon a non-water surface, comprising:
   100 parts by weight of a polymer selected from the group consisting of an ethylene-propylene copolymer, an ethylene-vinyl acetate copolymer, and combinations thereof, said ethylene-vinyl acetate copolymer having a weight average molecular weight of from about 40,000 to about 400,000 and the amount of said ethylene in said copolymer ranging from about 60 to about 95 percent by weight, said ethylene-propylene copolymer having a weight average molecular weight of from about 50,000 to about 250,000, and the amount of said ethylene in said copolymer ranging from about 30 to about 80 percent by weight; and
   a non-volatile insecticide, said insecticide selected from the group consisting of O,O-diethyl-O-(2-isopropyl-6-methyl-5-pyrimidinyl)phosphorathioate and 2-(1-methylethoxy)phenol methylcarbamate, the amount of said insecticide ranging from about 0.2 to about 40 parts by weight.

2. A slow release insecticide-containing polymer composition according to claim 1, wherein the amount of ethylene in said ethylene-vinyl acetate copolymer ranges from about 80 percent to about 94 percent by weight and the melt flow index ranges from about 6 to about 12, and wherein the amount of ethylene in said ethylene-propylene copolymer ranges from about 45 to about 75 percent by weight and wherein said ethylene-propylene copolymer has a melt flow index of from about 15 to about 45.

3. A slow release insecticide-containing polymer composition according to claim 2, wherein the molecular weight of said ethylene-vinyl acetate copolymer ranges from about 75,000 to about 300,000, wherein the molecular weight of said ethylene-propylene copolymer ranges from about 100,000 to about 200,000.

4. A slow release insecticide-containing polymer composition according to claim 3, wherein the amount of said insecticide ranges from about 2 to about 35 parts by weight.

5. A slow release insecticide-containing polymer composition according to claim 4, wherein said ethylenevinyl acetate copolymer has a melt flow range of from about 7 to about 11 and wherein said ethylene-propylene copolymer has a melt flow range of from about 20 to about 32.

6. A slow release insecticide-containing polymer composition according to claim 1, including from about 2 to about 25 parts by weight of an attractant agent.

7. A slow release insecticide-containing polymer composition according to claim 6, wherein said attractant compound is selected from the group consisting of soy oil and lecithin.

8. A slow release insecticide-containing polymer composition according to claim 7, wherein the amount of ethylene in said ethylene-vinyl acetate copolymer ranges from about 80 percent to about 94 percent by weight and the melt flow index ranges from about 6 to about 12, and wherein the amount of ethylene in said ethylene-propylene copolymer ranges from about 45 to about 75 percent by weight and wherein said ethylene-propylene copolymer has a melt flow index of from about 15 to about 45.

9. A slow release insecticide-containing polymer composition according to claim 8, wherein said molecular weight of said ethylene-vinyl acetate copolymer ranges from about 75,000 to about 300,000, and wherein said molecular weight of said ethylene-propylene copolymer ranges from about 100,000 to about 200,000.

10. A slow release insecticide-containing polymer composition according to claim 9, wherein the amount of said insecticide ranges from about 2 to about 35 parts by weight.

11. A slow release insecticide-containing polymer composition according to claim 9, wherein said ethylene-vinyl acetate copolymer has a melt flow range of from about 7 to about 11 and wherein said ethylene-propylene copolymer has a melt flow range of from about 20 to about 32.

12. A slow release insecticide-containing polymer composition according to claim 11, wherein the amount of said soy oil and lecithin ranges from about 4 parts to about 16 parts by weight.

13. A slow release insecticide-containing polymer composition according to claims 3, 5, 6, 7, 12, or 10, including a low density polyethylene having a molecular weight of from about 100,000 to about 400,000, the amount of said low density polyethylene polymer by weight based upon the total weight of said polymers ranging from about 30 percent to about 75 percent.

14. A process for dispensing an insecticide from an insecticide-containing polymer composition over a period of time, comprising distributing said insecticide-containing polymer composition of claim 1 over a non-water surface.

15. A process according to claim 14, wherein the amount of ethylene in said ethylene-vinyl acetate copolymer ranges from about 80 percent to about 94 percent by weight and the melt flow index ranges from about 6 to about 12, and wherein the amount of ethylene in said ethylene-propylene copolymer ranges from about 45 to about 75 percent by weight and wherein said ethylene-propylene copolymer has a melt flow index of from about 15 to about 45.

16. A process according to claim 15, wherein the molecular weight of said ethylene-vinyl acetate copolymer ranges from about 75,000 to about 300,000 and wherein the molecular weight of said ethylene-propylene copolymer ranges from about 100,000 to about 200,000.

17. A process according to claim 16, wherein said amount of insecticide ranges from about 2 parts to about 35 parts by weight and wherein said ethylene-vinyl acetate copolymer has a melt flow range of from about 7 to about 11, and wherein said ethylene-propylene copolymer has a melt flow range of from about 20 to about 32.

18. A process according to claim 14, including from about 2 to about 25 parts by weight of an attractant agent.

19. A process according to claim 18, wherein said attractant compound is selected from the group consisting of soy oil and lecithin.

20. A process according to claim 19, wherein the amount of ethylene in said ethylene-vinyl acetate copolymer ranges from about 80 percent to about 94 percent by weight and the melt flow index ranges from about 6 to about 12, and wherein the amount of ethylene in said ethylene-propylene copolymer ranges from about 45 to about 75 percent by weight and wherein said ethylene-propylene copolymer has a melt flow index of from about 15 to about 45, wherein the molecular weight of said ethylene-vinyl acetate copolymer ranges from about 75,000 to about 300,000 and wherein the molecular weight of said ethylene-propylene copolymer ranges from about 100,000 to about 200,000.

21. A process according to claim 20, wherein said amount of insecticide ranges from about 2 parts to about 35 parts by weight, wherein said ethylene-vinyl acetate copolymer has a melt flow range of from about 7 to about 11, and wherein said ethylene-propylene copolymer has a melt flow range of from about 20 to about 32.

22. A process according to claim 20, wherein the amount of said soy oil and lecithin ranges from about 4 parts to about 16 parts by weight.

23. A process according to claims 15, 16, 17, 18, 19, 22, or 21, including adding a low density of polyethylene having a molecular weight of from about 100,000 to about 400,000, the amount of said low density polyethylene polymer by weight based upon the total weight of said polymers ranging from about 30 percent to about 75 percent.

* * * * *